United States Patent [19]
Nicolaou et al.

[11] Patent Number: 6,043,382
[45] Date of Patent: Mar. 28, 2000

[54] TRANSFORMATIONS OF TAXOL

[75] Inventors: K.C. Nicolaou, La Jolla; Philippe G. Nantermet, San Diego; Rodney K. Guy, San Diego; Hiroaki Ueno, San Diego, all of Calif.

[73] Assignee: The Scripps Research Institute, La Jolla, Calif.

[21] Appl. No.: 09/123,504

[22] Filed: Jul. 28, 1998

Related U.S. Application Data

[62] Division of application No. 08/626,112, Apr. 1, 1996, Pat. No. 5,786,489, which is a division of application No. 08/193,263, Feb. 8, 1994, Pat. No. 5,504,222, which is a continuation-in-part of application No. 08/110,095, Aug. 20, 1993, Pat. No. 5,440,057.

[51] Int. Cl.⁷ .................................................. C07D 305/14
[52] U.S. Cl. ........................................... 549/510; 549/511
[58] Field of Search ....................................... 549/510, 511

[56] References Cited

U.S. PATENT DOCUMENTS

| | | | |
|---|---|---|---|
| 5,440,057 | 8/1995 | Nicolaou et al. | 549/511 |
| 5,504,222 | 4/1996 | Nicolaou et al. | 549/511 |

*Primary Examiner*—Ba K. Trinh
*Attorney, Agent, or Firm*—Donald G. Lewis

[57] ABSTRACT

A method for esterifying C13 deoxy taxoid intermediates employs three steps, i.e., oxygenation of the C13 deoxy taxoid intermediate to produce a C13 enone taxoid intermediate; reduction of the C13 enone to produce an alcohol; followed by esterification of the C13 alcohol. Key intermediates include C13 deoxy taxoids; C13 enone substituted taxoids; and C1–C2 cyclo carbonate esters of taxoids.

5 Claims, 2 Drawing Sheets

2: 10-deacetyl baccatin III

1: taxol

TRANSFORMATIONS OF TAXOL

CROSS-REFERENCE TO RELATED APPLICATION

The present application is a divisional application of U.S. patent application Ser. No. 08/626,112, filed Apr. 1, 1996, which issued on Jul. 28, 1998 as U.S. Pat. No. 5,786,489, which is a divisional application of U.S. patent application Ser. No. 08/193,263, filed Feb. 8, 1994, which issued on Apr. 2, 1996 as U.S. Pat. No. 5,504,222, which is a continuation-in-part of U.S. patent application Ser. No. 08/110,095, filed Aug. 20, 1993, which issued on Aug. 8, 1995 as U.S. Pat. No. 5,440,057, the disclosure of which is incorporated herein by reference.

FIELD OF INVENTION

The invention relates to taxol and to the synthesis of taxol analogs. More particularly, the invention relates to processes and key intermediates for synthesizing taxol analogs.

BACKGROUND

Taxol is a natural product with anti-cancer activity. Because natural sources of taxol are limited, synthetic methods e for producing taxol have been developed, e.g., K. C. Nicolaou et al., *J. Chem. Soc., Chem. Commun.* 1992, 1117–1118, *J. Chem. Soc., Chem. Commun.* 1992, 1118–1120, and *J. Chem. Soc., Chem. Commun.* 1993, 1024–1026. Several synthetic taxol analogs have also been developed and have been found to have altered chemical and biological activity as compared to natural taxol, e.g., K. C. Nicolaou et al., *Nature,* 1993, 364, 464–466. There is considerable interest in the design and production of further e taxol analogs. However, progress with respect to the synthesis of such taxol analogs has been blocked by a lack of information regarding certain key synthetic methods and key intermediates essential for the production of a wide range of taxol analogs.

What is needed is the identification of key synthetic methods and key intermediates for producing taxol analogs having altered activities.

SUMMARY

One aspect of the invention is directed to a method for esterifying taxoid intermediates having an ABCD ring skeleton structure with ring carbons C1–C15 and C20 represented by the following structure:

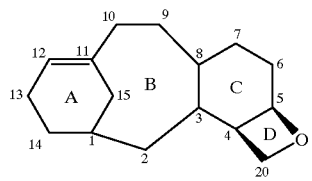

wherein the C13 carbon is a deoxy carbon. The method employs includes at least three steps. In the first step, the deoxy C13 of the taxoid molecule is oxygenated to form a C13 ketone. Pyridinium chlorochromate is a preferred oxidant for performing this process. In the second step, the C13 ketone produced in the first step is reduced to form a C13 alcohol. Sodium borohydrate is a preferred reductant to form an alcohol from the C13 ketone. In the third step, C13 alcohol formed in the second step is esterified. A preferred method of esterification employs a β-lactam intermediate as taught by Ojima (Ojima, I. et al., *Tetrahedron* 1992, 48, 6985 and *Tetrahedron Lett.* 1993, 34, 4149) and by Holton, R. (European Patent Application No. EP 400,971 (1990) and *Chem Abstracts* 1990, 114, 164568q).

An alternative aspect of this invention is directed to an improved taxoid intermediate having an ABCD ring skeleton structure with ring carbons C1–C15 and C20 as indicated above wherein the C1 and C2 carbons are incorporated within a cyclo carbonate ester. An example of such an improved taxoid intermediate is indicated below:

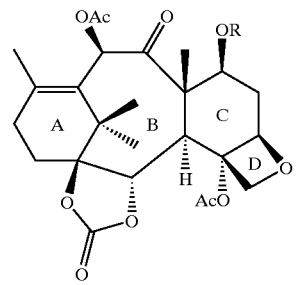

wherein R is selected from the group consisting of H and a protective group for hydroxyls.

A further aspect of the invention is directed to an improved taxoid intermediate having an ABCD ring skeleton structure with ring carbons C1–C15 and C20 the C13 carbon is a deoxy carbon. Examples of a C13 deoxy taxoid intermediate is provided below:

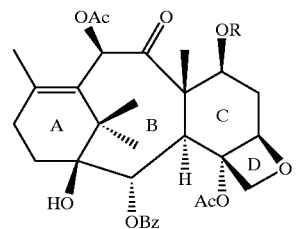

wherein R is selected from the group consisting of H and a protective group for hydroxyls.

Another alternative aspect of this invention is directed an improved taxoid intermediate having an ABCD ring skeleton structure wherein the C13 carbon includes a ketone substitution and forms an enone with the C12–C11 bridgehead double bond. An example of this aspect of the invention is illustrated by the following structure:

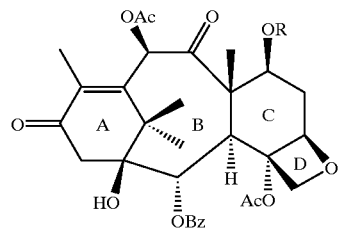

wherein R is a protective group for hydroxyls, preferably $SiEt_3$.

DETAILED DESCRIPTION

Chemistry is disclosed which defines chemical pathways via which taxol 1 and 10-deacetyl baccatin III 2 (Indena Company, Italy) can be converted to a variety of intermediates including compounds 4–6 and 12–15, all of which can then be converted back to taxol 1. These reactions can be employed in the preparation of taxol analogs and in the total synthesis of taxol.

Figure 1A:
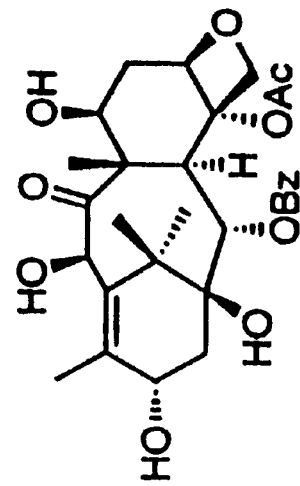
FIGS. 1A and 1B illustrate degradative and synthetic plans for producing taxoid intermediates from naturally occurring 10-deacetyl baccatin III (2) and for converting such taxoid intermediates to taxol (1).
Figure 1A:
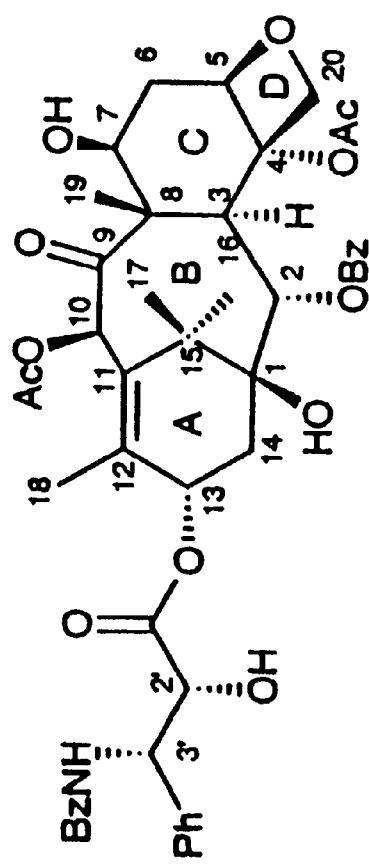
Figure 1B:
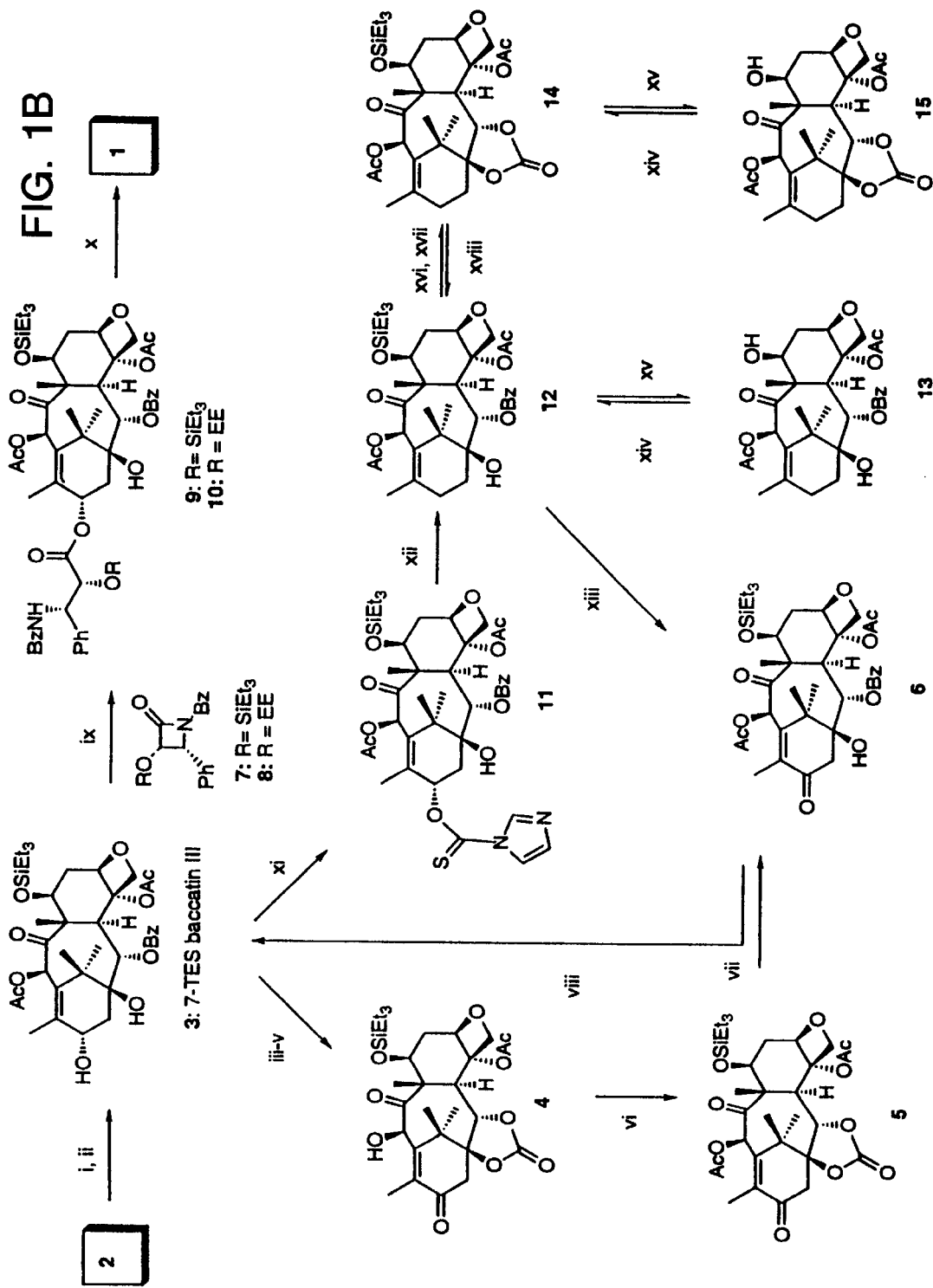

Initially, a C1–C2 vicinal diol was prepared in order to study the introduction of protecting groups at the C2 position and their conversion to the C1 hydroxy-C2 benzoate. To this end, 7-SiEt$_3$ baccatin III (3) was prepared from 10-deacetyl baccatin III (2) according to the methods of Magri et al (*Journal of Organic Chemistry* 1986, 51, p. 3239) and of Denis et al. (*Journal of the American Chemical Society* 1988, 110, p. 5917), as shown in FIG. 1. All attempts to selectively deprotect the C2 and C10 hydroxyl groups, including basic hydrolysis and metal hydride reductions, produced only low yields of the desired triol. It was then postulated that oxidation of the C13 hydroxyl group would remove a possible hydrogen bond between that hydroxyl and the C4 acetate, thus rendering the C4 acetate less susceptible to hydrolysis or intramolecular attack from the C2 hydroxyl group. Indeed, TPAP oxidation of compound 3, according to the method of Griffith (*Aldrichim. Acta,* 1990, 23, 13), provided the corresponding C13 ketone, in 98% yield. This was readily hydrolyzed under basic conditions to provide the corresponding C1–C2-vicinal diol with an 81% yield.

Modeling studies (Nicolaou et al., *J. Chemical Society, Chem. Communications,* 1992, p. 1118) suggest the benefit of using a cyclic protecting group for the C1–C2 diol in order to preorganize the molecular skeleton prior to ring closure to form the 8-membered ring. Furthermore, with the goal of selectively introducing the C2 benzoyl group in the synthetic direction, we found that it is possible to directly convert a C1–C2 carbonate ester into a C2 benzoate by addition of a nucleophilic reagent carrying a phenyl group. Treatment of the triol resulting from the oxidation/hydrolysis of 3 with a phosgene in pyridine, did indeed provide the desired carbonate 4 with a yield of 65%. The acetate 5 was then prepared from 4 using standard acetylation conditions. This intermediate (5) served admirably as a precursor of taxol (1) as described below.

Treatment of carbonate 5 with excess PhLi at −78° C. for 10 minutes resulted in the regioselective formation of the benzoate 6 with a yield, according to chromatographic and spectroscopic analysis, of 70%. A small amount (approximately 1-%) of the 10-deacetyl product resulting from PhLi attack on the C10 acetate group was also observed, although treatment of the crude reaction mixture with Ac$_2$O in the presence of DMAP provided 6 as a single product, raising the yield of the 5 to 6 step to 80%. This chemistry provided a convenient protecting device for the C1–C2 diol group and opened directed access to the C1 hydroxyl/C2 benzoate system of taxol. The use of other nucleophilic reagents carrying other than phenyl groups to selectively open this carbonate ring should provide a variety of C2 ester, a class of derivatives which is otherwise difficult to obtain from naturally occurring taxoids. The remarkable resistance of the other four carbonyl functionalities in compound 5 towards PhLi is presumably due to steric shielding of these sites. Conversion of enone 6 back to taxol (1) was then demonstrated by the following sequence. Regio- and stereoselective reduction of the C13 carbonyl group was achieved with NaBh$_4$, resulting in the formation of 7-TES (SiEt$_3$) baccatin III (3) in 83% yield, according to the method of Kingston, (*Pharmac. Ther.* 1991, 52, p. 1). Attachment of the side chain onto intermediate 3 was then accomplished using Ojima's method, i.e., Ojima, et al., *Tetrahedron* 1992, 48, 6985 and *Tetrahedron Lett.* 1993, 34, 4149 and Holton, R., European Patent Application No. EP 400,971, filed 1990 and *Chem Abstracts* 1990, 114, 164568q. Thus optically active β-lactams 7 and 8 were coupled with 3 using NaN(SiMe$_3$)$_2$, to provide 2',7-diprotected taxol intermediates 9 and 10 respectively. Deprotection of either of these compounds (9 or 10) using standard conditions provided taxol 1 with a overall yield from 3 of approximately 70%.

Anther possible step in a potential total synthesis of taxol 1 is the oxidation of the C13 methylene to a ketone group. To test this hypothesis, the C13 deoxy compound 12 was prepared from 3, via the thionoimidozolide 11, using Barton's deoxygenation procedure, i.e., thiocarbonyldiimidazole-DMAP, heat, 86%, followed by Bu$^n_3$SnH-AIBN, heat, 40%. (Barton, *J. Chem. Soc., Perkin I* 1975, p. 1574 and Hartwig, *Tetrahedron* 1983, 39, p. 2609.) A substantial amount, approximately 25%, of the corresponding C12–C13 alkene was also isolated in this deoxygenation reaction. Enone 6 was then prepared from 12, with a yield of 75%, using pyridinium chlorochromate (PCC) in refluxing benzene. In order to penetrate further into the projected synthetic scheme, the 7-hydroxy compound 13 was prepared from 12 by desilylation (HF.pyr, 65%). Conversion of compound 13 back to 12 was accomplished using Et$_3$SiCl in pyridine, with a yield of 85%.

Compound 12 was also converted to carbonate 14 using similar chemistry as described for the synthesis of 4, i.e., K$_2$CO$_3$ in MeOH/H$_2$O/THF, 85% based on 55% conversion followed by phosgene in pyridine, 95%. Desilylation of 14 (HF.pyr, 88%) led to the 7-hydroxy compound 15 which was converted back to 14 by silylation under standard conditions, i.e., Et$_3$SiCl-pyr, 85%. Nucleophilic addition of PhLi to the carbonate 14 as described above provided the benzoate 12 with a yield of 80%.

Reagents and Conditions:

The reagents and conditions for the reactions indicated in FIG. 1 are provided below:

(i) To 10-deacetyl baccatin III 2 is added 20 equivalents of Et$_3$SiCl in pyridine at 25° C. for 20 hours to produce the TES (SiEt$_3$) intermediate with a yield of 89%.

(ii) To the TES product of (i) is added 5 equivalents of AcCl in pyridine at 0° C. for 48 hours to produce 7-TES baccatin III 3 with a yield of 90%.

(iii) To the product of (iii) is added 0.05 equivalents of (Pr$^n$)$_4$NRuO$_4$, 1.5 equivalents of 4-morpholine N-oxide, 4 Å molecular sieves in acetonitrile for 30 minutes with a yield of 98%.

(iv) To the product of (iii) is added K$_2$CO$_3$ cat., in MeOH, H$_2$O at 0° C. for 9 hours with a yield of 81%.

(v) To the product of (iv) is added 10 equivalents of phosgene in pyridine at 25° C. for 30 minutes to produce compound 4 with a yield of 65%.

(vi) To compound 4 is added 10 equivalents of Ac$_2$O and 20 equivalents of 4-dimethylaminopyridine in Ch$_2$Cl$_2$ for 30 minutes to produce compound 5 with a yield of 95%.

(vii) To compound 5 is added 5 equivalents of PhLi in TNF at −78° C. for 10 minutes to produce compound 6 with a yield of 70% plus 10% 10-deacetyl 6.

(viii) To compound 6 is added 10 equivalents of NaBH₄ in MeOH at 25° C. for 5 hours to produce compound 3 with a yield of 83%.

(ix) To compound 3 is added 3.5 equivalents of 7 or 8 and 3 equivalents of NaN(SiMe₃)₂ in THF at 0° C. for 30 minutes to produce compounds 9 or 10 respectively with a yield of 87% based upon 90% conversion.

(x) To compound 9 is added HF pyridine in THF at 25° C. for 1.25 hours to produce compound 1 with a yield of 80%. To compound 10 is added EtOh, 0.5% HCl at 0° C. for 72 hours to produce compound 1 with a yield of 80%.

(xi) To compound 3 is added 20 equivalents of thiocarbonyldiimidazole and 30 equivalents of 4-dimethylaminopyridine in THF in sealed tubes at 75° C. for 18 hours to produce compound 11 with a yield of 86%.

(xii) To compound 11 is added 20 equivalents of Bu"₃SnH, AIBN cat., in toluene at 65° C. to produce compound 12 with a yield of 40%, plus 25% of C12–C13 alkene.

(xiii) To compound 12 is added 30 equivalents of pyridiniumchlorochromate, NaOAc, Cellite in refluxing benzene to produce compound 6 with a yield of 75%.

(xiv) To compound 12 or 14 is added HF.pyridine in THF at 25° C. for 1 hour to produce compound 13 with a yield of 65% or to produce compound 15 with a yield of 88%.

(xv) To compound 13 is added 20 equivalents of Et₃SiCl in pyridine at 25° C. for 20 hours to produce compound 12 with a yield of 85%.

(xvi) To compound 12 is added K₂CO₃ cat. in MeOH/H₂O/THF at 0° C. for 9 hours with a yield of 85% based on 55% conversion.

(xvii) To the product of (xvi) is added 10 equivalents of phosgene in pyridine at 25° C. for 30 minutes to produce 14 25 with a yield of 95%.

(xviii) To compound 14 is added 5 equivalents of PhLi in THF at −78° C. for 10 minutes to produce 12 with a yield of 80%.

Definitions: TES=SiEt₃; Bz=COC₆H₅; Ac=COCH₃; EE=ethoxyethyl.

Physical Characterization:

All new compounds exhibited satisfactory spectral and analytical and/or exact mass data. yields refer to chromatographically and spectroscopically homogeneous materials. Selected physical data is presented as follows:

4: Rf=0.31 (silica, 25% EtOAc in light petroleum); IR (film)=$v_{max}$/cm$^{-1}$ 2926, 1622, 1754, 1732, 1689; $^1$H NMR (500 MHz, CDCl₃); δ 6.52 (s, 1H, 10-H), 4.89 (d, J 9 Hz, 1H, 5-H), 4.60 (d, J 9 Hz, 1H, 20a-H), 4.48 (d, J 5.5 Hz, 1H, 2-H), 4.45 (d, J 9 Hz, 1H, 20b-H), 4.42 (m, 1H, 7-H), 3.49 (d, J 5.5 Hz, 1H, 3-H), 2.90 (d, J 20 Hz, 1H, 14a-H), 2.79 (d, J 20 Hz, 1H, 14b-H), 2.56 (m, 1H, 6a-H), 2.19 (s, 3H, OAc), 2.16 (s, 3H, oAc), 2.07 (s, 3H, 18-CH₃), 1.87 (m, 1H, 6b-H), 1.71 (s, 3H, 19-CH₃), 1.28 (s, 3H, 16-CH₃), 1.26 (s, 3H, 17-CH₃), 0.89 (t, J 8 Hz, 9H, SiEt₃), 0.55 (m, 6H, SiEt₃); $^{13}$C NMR (125 MHz, CDCl₃) 200.2, 195.7, 170.5, 166.7, 152.0, 150.4, 142.5, 88.2, 83.9, 79.8, 76.6, 75.7, 71.5, 61.0, 43.1, 41.6, 39.8, 37.7, 31.6, 29.7, 21.5, 20.7, 18.4, 14.4, 9.7, 6.7, 5.1; HRMS (FAB) Calcd. for C₃₁H₄₄O₁₁Si (M+H⁻): 621.2731; found 621.2745.

6: Rf=0.5 (silica, 50% EtOAc in light petroleum); IR (film)=$v_{max}$/cm$^{-1}$ 3499, 2956, 1758, 1732, 1673, 1657, 1604; $^1$H NMR (500 MHz, CDCl₃) δ 8.05 (c, J 7.3 Hz, 2H, OBz), 7.61 (t, J 7.5 Hz, 1H, OBz), 7.47 (t, J 7.8 Hz, 2H, OBz), 6.57 (s, 1H, 10-H), 5.67 (d, J 6.7 Hz, 1H, 2-H), 4.90 (d, J 8.4 Hz, 1H, 5-H), 4.46 (dd, J 10.4, 6.8 Hz, 1H, 7-H), 4.31 (c, J 8.5 Hz, 1H, 20a-H), 4.09 (d, J 8.5 Hz, 1H, 20b-H), 3.89 (c, J 6.7 Hz, 1H, 3-H), 2.92 (d, J 19.9 Hz, 1H, 14a-H), 2.63 (d, J 19.9 Hz, 1H, 14b-H), 2.50 (m, 1H, 6a-H:), 2.21 (s, 3H, OAc), 2.17 (s, 3H, OAc), 2.16 (s, 3H, 18-CH₃), 1.82 (m, 1H, 6b-H), 1.65 (s, 3H, 19-CH₃), 1.25 (s, 3H, 16-H), 1.17 (s, 3H, 17-H). 0.90 (t, J 7.9 Hz, 9H, SiEt₃), 0.58 (m, 6H, SiEt₃); $^{13}$C NMR (125 MHz, CDCl₃); δ 200.2, 198.3, 170.1, 168.9, 166.8, 153.0, 140.2, 133.9, 130.0, 128.8, 128.7, 83.9, 80.5, 78.4, 76.1, 76.0, 72.8, 72.2, 59.4, 46.2, 43.4, 42.4, 37.1, 33.0, 21.7, 21.0, 18.2, 13.5, 9.5, 6.7, 5.1; HRMS (FAB): Calcd. for C₃₇H₅₀O₁₁Si (M+H⁻): 699.3201; found 699.3220.

13: Rf=0.35 (silica, 50% -EtOAc in light petroleum); IR (film)=$v_{max}$/cm$^{-1}$ 3503, 2924, 2853, 1728, 1713; $^1$H NMR (500 MHz, CDCl₃); δ 8.06 (d, J 7.3 Hz, 2H, OBz), 7.58 (t, J 7.5 Hz, 1H, OBz), 7.45 (t, J 10 Hz, 2H, OBz), 6.31 (s, 1H, 10-H), 5.58 (d, J 6.5 Hz, 1H, 2-H), 4.98 (d, J 7.5 Hz, 1H, 5-H), 4.44 (dd, J 11.0, 7.0 Hz, 1H, 7-H), 4.30 (d, J 8.0 Hz, 1H, 20a-H), 4.14 (d, J 8.0 Hz, 1H, 20b-H), 3.76 (d, J 6.5 Hz, 1H, 3-H), 2.71 (m, 1H, 13a-H), 2.55 (m, 1H, 13b-H), 2.29 (s, 3H, OAc), 2.25 (m, 1H), 2.23 (s, 3 H, OAc), 1.95 (s, 3H, 18-CH₃), 1.92 (m, 1H), 1.85 (m, 1H), 1.69 (m, 1H), 1.64 (s, 3H, 19-CH₃), 1.11 (s, 3H, 16-H), 1.09 (s, 3H, 17-H); $^{13}$C NMR (125 MHz, CDCl₃); 204.4, 171.5, 169.8, 166.9. 144.0, 133.7, 131.3, 130.0, 129.3, 128.6, 84.22, 81.32, 80.97, 76.35, 73.95, 72.39 65.86, 58.89, 45.89, 42.14, 35.71, 30.19, 29.69, 26.58, 25.30, 22.08, 20.96, 19.61, 15.27, 9.08; HRMS (FAB): Calcd for C₃₁H₃₈O₁₀ (M+Na⁻): 593.2363; found 593.2360.

14: Rf=0.82 (silica, 50% EtOAc in light petroleum); IR (film)=$v_{max}$/cm$^{-1}$ 2924, 1814, 1728, 1461, 1372, 1238; $^1$H NMR (500 MHz, CDCl₃); δ 6.40 (s, 1H, 10-H), 4.95 (d, J 9.0 Hz, 1H, 5-H), 4.60 (d, J 9.0 Hz, 1H, 20a-H), 4.47 (d, J 9.0 Hz, 1H, 20b-H), 4.43 (dd, J 10.0, 7.5 Hz, 1H, 7-H), 4.39 (d, J 5.5 Hz, 1H, 2-H), 3.36 (d, J 5.5 Hz, 1H, 3-H), 2.71 (m, 1H, 13a-H), 2.56 (m, 1H, 13b-H), 2.17 (s, 3H, OAc), 2.15 (s, 3H, OAc), 2.12 (m, 1H), 2.07 (s, 3H, 18-CH₃), 1.97 (m, 1H), 1.88 (m, 2H), 1.78 (s, 3H, 19-CH₃), 1.23 (s, 3H, 16-CH₃), 1.17 (s, 3H, 17-CH₃), 0.88 (t, J 7.5 Hz, 9H, OSiEt₃), 0.55 (dq, J 8.0, 3.0 Hz, 6H, —OSiEt₃); $^{13}$C NMR (125 MHz, CDCl₃); 202.6, 170.3, 169.2, 153.1, 144.0, 130.7, 92.8, 84.0, 80.3, 80.0, 76.4, 76.1, 60.3, 43.5, 38.0, 29.7, 29.4, 25.5, 23.1, 21.9, 21.1, 19.1, 9.8, 6.7, 5.2; HRMS (FAB) Calcd. for C₃₁H₄₆O₁₀Si (M+Cs⁻): 739.1915; found 739.1929.

What is claimed is:

1. A method for esterifying a taxoid intermediate represented by the following structure:

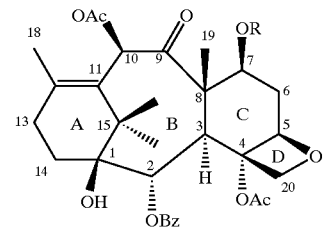

wherein R is selected from the group consisting of H and a protective group for hydroxyls and wherein the C13 carbon is a deoxy carbon, the method comprising the following steps:

Step A: oxygenating the C13 deoxy carbon to form a C13 enone; then

Step B: reducing the C13 enone to form a C13 alcohol; and then

Step C: esterifying the C13 alcohol.

2. A method for esterifying a taxoid intermediate as disclosed by claim 1 wherein:

in said Step A, the C13 deoxy carbon is oxygenated to form the C13 enone with pyridinium chlorochromate.

3. A method for esterifying a taxoid intermediate as disclosed by claim 1 wherein:

in said Step B, the C13 enone is reduced to the C13 alcohol with sodium borohydrate.

4. A method for esterifying a taxoid intermediate as disclosed by claim 1 wherein:

in said Step C, the C13 alcohol is esterified using a β-lactam intermediate.

5. A method for esterifying a taxoid intermediate according to claim 1 wherein R is $SiEt_3$.

* * * * *